United States Patent [19]

Proctor

[11] Patent Number: 5,034,515

[45] Date of Patent: Jul. 23, 1991

[54] STAPHYLOCOCCAL FIBRONECTIN RECEPTOR, MONOCLONAL ANTIBODIES THERETO AND METHODS OF USE

[75] Inventor: Richard A. Proctor, Madison, Wis.

[73] Assignee: Wisconsin Alumni Research Foundation, Madison, Wis.

[21] Appl. No.: 99,756

[22] Filed: Sep. 22, 1987

[51] Int. Cl.$^5$ .................. C07H 1/00; C07H 15/22; C07H 17/02; C07H 1/06

[52] U.S. Cl. .................. 536/1.1; 536/14; 536/17.2; 536/127; 536/128

[58] Field of Search .............. 536/1.1, 14, 14.2, 127, 536/128

[56] References Cited

U.S. PATENT DOCUMENTS 4,197,290  4/1980  Yoshida .......................... 424/92

OTHER PUBLICATIONS

Proctor, Richard A., The Staphylococcal Fibronectin Receptor: Evidence for Its Importance in Invasive Infections, Reviews of Infectious Diseases, vol. 9, Supplement 4, Jul.-Aug. 1987, pp. S335-S340.

Proctor, Richard A. et al., Fibronectin Mediates Attachment of Staphylococcus aureus to Human Neutrophils, Blood, vol. 59, No. 4, Apr. 1982, pp. 681-687.

Proctor, Richard A. et al., Subinhibitory Concentrations of Antibiotics Alter Fibronectin Binding to Staphylococcus aureus, Antimicrobial Agents and Chemotherapy, vol. 24, No. 5, Nov. 1983, pp. 823-826.

Proctor, Richard A. et al., Effects of Subinhibitory Concentrations of Antibiotics on Staphylococcus aureus Interactions with Fibronectin, Journal of Antimicrobial Chemotherapy (1983) 12, Suppl. C. 85-95.

Mosher, Deane F. et al., Fibronectin: Role in Inflammation, Advances in Inflammation Research, vol. 2, 1981, pp. 187-207.

Mosher, Deane F., et al., Binding and Factor XIII$_a$—Mediated Cross-Linking of a 27-Kilodalton Fragment of Fibronectin to Staphylococcus aureus, Science, vol. 209, Aug. 1980, pp. 927-929.

Proctor, Richard A. et al., Fibronectin Binding to Staphylococcus aureus, Journal of Biological Chemistry, vol. 257, No. 24, Dec. 1982, pp. 14788-14794.

Proctor, Richard A. et al., Fibronectin-induced Agglutination of Staphylococcus aureus Correlates with Invasiveness, The Journal of Laboratory and Clinical Medicine, vol. 104, No. 4, Oct. 1984, pp. 455-469.

Mitchell, J. Nelles, et al., Reactivity of Type-Specific Monoclonal Antibodies with Staphylococcus aureus Clinical Isolates and Purified Capsular Polysaccharide, Infection and Immunity, vol. 49, No. 1, Jul. 1985, pp. 14-18.

Hochkeppel, H. K. et al, Serotyping and Electron Microscopy Studies of Staphylococcus aureus Clinical Isolates with Monoclonal Antibodies to Capsular Polysaccharide Types 5 and 8, Journal of Clinical Microbiology, vol. 25, No. 3, Mar. 1987, pp. 526-530.

Huycke, Mark M. et al., Specific Inhibition of Fibronectin (FN) Binding to a Staphylococcus aureus (Sa) FH Receptor (FNR).

Primary Examiner—Nathan M. Nutter
Attorney, Agent, or Firm—Quarles & Brady

[57] ABSTRACT

A purified fibronectin receptor polysaccharide derived from Staphylococcus aureus is useful as an antigen for diagnostic tests and the preparation of monoclonal antibodies. The fibronectin receptor polysaccharide is prepared by gently removing expresed material, including the polysaccharide, from the cell surfaces of the S. aureus without killing the cells followed by purification. Monoclonal antibodies directed against the polysaccharide can be used in methods of preventing or treating S. aureus infections by administering the monoclonal antibodies to animals.

3 Claims, No Drawings

STAPHYLOCOCCAL FIBRONECTIN RECEPTOR, MONOCLONAL ANTIBODIES THERETO AND METHODS OF USE

FIELD OF THE INVENTION

The invention relates generally to staphylococcal fibronectin receptors. More particularly, it relates to a method of collecting and purifying fibronectin receptor polysaccharide from a staphylococcal source and monoclonal antibodies thereto. Further, it relates to methods of treating or preventing diseases by blocking fibronectin receptors with the monoclonal antibodies and diagnostic tests employing the purified fibronectin receptor polysaccharide as an antigen.

BACKGROUND OF THE INVENTION

Over the past 7 years, the mechanisms by which *Staphylococcus aureus*, an infectious microorganism, adheres to host tissues has been studied because adherence is the first step in the development of an infection. If bacteria are unable to adhere to a surface, they will be swept away by the body fluids that normally bathe the tissues and an infection will not occur. Hence, adherence is the crucial first step in initiating and spreading infections. It is generally accepted that microorganisms adhere to surface components of the host tissues.

It has been found that *S. aureus* interacts with a host protein called "fibronectin." Fibronectin is a major component of the material found between cells and also in blood plasma. Fibronectin is essential to the well-being of the host as it serves as the "glue" which links one cell to another cell and plays a major role in wound healing.

There are several lines of evidence which suggest that fibronectin plays an important role in the adherence of *S. aureus* to host tissues. Supporting this concept are the following observations: (i) *S. aureus* has a specific receptor for fibronectin,* (ii) the *S. aureus* fibronectin receptor (FN-R) is expressed on the surface of the bacterium where it can interact with host tissues,* (iii) the fibronectin receptor is expressed in greater numbers on clinical isolates of *S. aureus* that have invaded the host as compared to noninvasive isolates,* (iv) purified FN-R decreases *S. aureus* interactions with fibronectin,* (v) antibodies directed against FN-R reduce fibronectin binding to *S. aureus*,* (vi) fibronectin is found at sites frequently infected by *S. aureus*, (vii) fibronectin enhances *S. aureus* adherence,* (viii) specific removal of fibronectin from a complex mixture of host proteins decreases *S. aureus* binding while removal of other proteins does not, and (ix) antibodies against fibronectin inhibit *S. aureus* binding to host tissues.

There also are data which suggest that the fibronectin receptor polysaccharide plays a major role in the initiation of *S. aureus* infections: (i) *S. aureus* mutants that are isogenic with the parent strain except for the ability to express fibronectin receptor colonize the heart valves of rats 120-fold less effectively than the parent strain* and (ii) a monoclonal antibody which recognizes the most invasive strains of *S. aureus* interacts preferentially with the fibronectin receptor.*

*Discovered in R.A. Proctor's laboratory

My article "The Staphylococcal Fibronectin Receptor: Evidence for Its Importance in Invasive Infections" in Reviews of Infectious Diseases Vol. 9, Supp. 4, §335 to §340 (July/August 1987) reviews the data that support the presence of a specific fibronectin receptor on *S. aureus* and discusses the criteria necessary to establish a role for fibronectin in pathogenesis of invasive staphylococcal infections.

The above article is incorporated by reference herein.

SUMMARY OF THE INVENTION

It is an object of the present invention to disclose a purified fibronectin receptor polysaccharide obtained from *Staphylococcus Aureus* and a method of obtaining it.

It is another object to disclose monoclonal antibodies directed to the fibronectin receptor polysaccharide.

It is still further an object to disclose methods of preventing or treating infections caused by *S. aureus* using the monoclonal antibodies.

It also is an object to disclose diagnostic methods which employ the purified fibronectin receptor polysaccharide as an antigen and the monoclonal antibodies.

I have discovered that a purified fibronectin receptor polysaccharide can be obtained from *Staphylococcus aureus* which is primarily a carbohydrate; it contains no lipids, and less than 2% protein. The sugars making up the polysaccharide are aminohexoses. The purified polysaccharide cross-reacts with monoclonal antibody directed against the type 8 capsular polysaccharide of *S. aureus* but the fibronectin receptor polysaccharide of the present invention contains no uronic acids and thus is distinct from type 8 capsular material. The fibronectin receptor polysaccharide of the present invention has an average molecular weight of ~60 kdal and it competes with intact organisms for fibronectin binding.

The method of the present invention for obtaining the fibronectin receptor polysaccharide comprises harvesting the polysaccharide from intact *Staphylococcus aureus* cells by gently releasing the surface material, including expressed fibronectin receptor polysaccharide, on the cells without rupturing or killing the cells by non-destructive procedures, such as gentle sonification. The polysaccharide is then purified by DEAE ion exchange and fibronectin affinity chromatography.

The monoclonal antibodies of the present invention are prepared by injecting the fibronectin receptor polysaccharide into mice, removing the spleens of the mice showing antibody that blocked fibronectin binding to FN-R, cloning the antibodies, preparing hybridomas by the method of Kohler and Milstein and selecting the monoclonal antibodies that demonstrate blocking activity and inhibit fibronectin binding to FN-R.

The monoclonal antibodies against the fibronectin receptor polysaccharide can be used in diagnostic tests employing the fibronectin receptor polysaccharide as an antigen to screen patients for anti-fibronectin receptor antibodies.

The monoclonal antibodies are also useful in methods of preventing or treating *S. aureus* infections in patients. In such methods safe and effective amounts of the monoclonal antibodies are administered to the patients.

Other objects and advantages of the invention will be apparent to those skilled in the art.

DESCRIPTION OF THE PREFERRED EMBODIMENT

In the preferred method of preparation, the fibronectin receptor polysaccharide is prepared by gently releasing the expressed material from the cell surfaces of *S. aureus* without killing the cells as hereinafter described.

Method of Preparation of Purified Fibronectin Receptor Polysaccharide

*S. aureus* is grown in chemically defined or dialyzed media for 16 hours. Bacteria are harvested by centrifugation, washed twice in Hank's balanced salt solution, and then once in sterile distilled water. The organisms are then resuspended in distilled water and gently sonicated (two, 2.5 minute bursts in a cup horn Heat Systems sonicator at 18–20% output). The sonication removes cell surface material without killing the *S. aureus*, as determined by no change in the viability counts and by lack of DNA release. The sonicated mixture is then centrifuged to remove bacteria. The supernatant is saved and lyophilized. The lyophilized material is then placed on a DEAE Sephadex column and eluted with a linear salt (NaCl) gradient. Fractions are collected and the presence of fibronectin receptor polysaccharide (FN-R) determined by competitive inhibition of radiolabeled fibronectin with *S. aureus* ATCC 25923. Fractions containing the FN-R are then passed through a G-200 Sephadex column. Fractions are collected as they come off this second column and the presence of FN-R determined. Those fractions containing the FN-R are then pooled and lyophilized. This material is purified approximately 1000-fold as compared to the starting material which was shed off the bacteria. The chemical characterization of this material shows that it is a polysaccharide which is less than 2% protein, contains no lipids, and is primarily carbohydrate. The sugars making up the carbohydrates are aminohexoses, but do not contain uronic acids. The FN-R has an average molecular weight of ~60kdal. This polysaccharide cross-reacts with monoclonal antibody directed at the type 8 capsular polysaccharide of *S. aureus*, but the chemical characterization shows that it is distinct from the type 8 capsular material which contains uronic acids.

The techniques reported in previous publications on a FN-R purification have relied on harvesting the bacteria from complex media and using broken open bacteria. This causes problems in the interpretation of validity of the material that has been harvested for two reasons. First, bacteria can adsorb complex media components onto their surface. The media used in the previous reports are made from crude digests of mammalian tissues and could quite possibly contain components which are known to interact with fibronectin (such as collagen and fibrin). The nonchemically defined media used in these previous reports contain many macromolecules which could stick to the surface of the *S. aureus* and be purified as if they were produced by the bacteria. Second, by using broken open *S. aureus*, many intracellular proteins are being released, some of which may interact with fibronectin, but they may not be expressed on the surface of the microorganism. It has been observed that broken open *S. aureus* contain many more fibronectin receptors than do intact bacteria. The fact that antibodies produced against the protein fibronectin receptor do not block fibronectin binding to *S. aureus* suggests that these protein materials are not the critical ligands for promoting fibronectin-*S. aureus* interactions. This is in contrast to antibodies which react with the carbohydrate FN-R of the present invention, wherein the binding of fibronectin is almost completely blocked. Hence, breaking open the bacteria may release fibronectin receptor materials which are not expressed normally. These "released" materials are different from the FN-R expressed on the outside of the bacteria. Consequently, the novel technique of harvesting the surface material without breaking open the bacteria prevents the harvesting of potentially nonexpressed, non-surface fibronectin receptor material. Thus, the harvesting techniques are unique and have led to the isolation of a carbohydrate FN-R polysaccharide which is important in the pathogenesis of *S. aureus* infections.

Production of Monoclonal Antibodies Against The Fibronectin Receptor Polysaccharide The FN-R polysaccharide obtained by the above method was used as an antigen to prepare monoclonal antibodies. One hundred micrograms of the antigen was mixed with complete Freund's adjuvant and injected subcutaneously into multiple sites on BALB/c mice. The mice were then injected with 100 µg of antigen intraperitoneally after 2 and 4 weeks. At 6 weeks, the mice were injected with 100 µg intravenously. Two and three days later, the mice were given 100 µg of antigen intraperitoneally. The mice were bled and those showing blocking antibody (antibody which blocked fibronectin binding to the FN-R in the ELISA test) had their spleens removed. After screening approximately 800 clones, several clones were made into hybridomas by fusing the clones with cancerous tumor cells (NS-1 cells) derived from myeloma tumors of bone marrow after the method of Kohler and Milstein. The hybridomas were screened to select ones producing the desired antibody and grown in culture to produce monoclonal antibodies. Seven monoclonal antibodies were produced which demonstrated blocking activity. Two monoclonal antibodies gave 70–92% inhibition of fibronectin binding to the FN-R in an ELISA assay when these antibodies were diluted 1:100.

Diagnostic Assay (ELISA) for Determining the Presence of Anti-FN-R Antibodies in Patients' Sera The FN-R polysaccharide employed was harvested from the surface of a strain expressing large numbers of FN-R (*S. aureus* strain 6850) (ATCC No. 53657). This strain was discovered by screening several hundred strains of *S. aureus*. The FN-R polysaccharide was purified as described above. The lyophilized polysaccharide was resuspended in distilled water to a concentration of 1 mg/ml. It was then tested for inhibitory activity in a standard binding assay and adjusted to a concentration that gave 50% inhibition of 3 µg 125 I-labeled fibronectin binding to $5 \times 10^8$ *S aureus* ATCC 25923 (this is generally about 1 µg of polysaccharide.) Then 10µg of this FN-R polysaccharide which was to serve as the antigen was placed in each well of a 96 well microtiter plate and allowed to dry overnight. Antibody, either from the patient's serum or added as control, was then added to the well. Sera were pretreated with gelatin-Sepharose to remove plasma fibronectin. One microgram of fibronectin was then added to each well. After a 60 minute incubation at room temperature, the wells are washed and an alkaline phosphatase conjugated to rabbit anti-fibronectin monoclonal antibody is added. After incubation, the wells were washed again and the appropriate substrate is added.

The test is read fluoroscopically. If the patient's serum has no antibody, then the maximal value will be recorded. However, if there is specific antibody present, then this will interfere with fibronectin binding to the FN-R polysaccharide and will give a lower optical fluorescent reading. A direct inverse relationship between antibody concentration and fluorescence obtains which can be used to determine antibody titer. It has been found that antibodies to the FN-R displace the fibronectin binding to the well and that fibronectin concentrations of 1 μg are sufficient to saturate all the receptors in the well.

This competitive ELISA test and similar diagnostic tests employing the FN-R polysaccharide or the monoclonal antibodies are useful in predicting which patients are at high risk for developing invasive *S. aureus* infections.

The microorganism, *S. aureus*, is a potent infectious pathogen. Interactions between host fibronectin and the *S. aureus* FN-R play an important role in the initiation of infections. Because antibodies directed against the FN-R polysaccharide block binding of fibronectin to *S. aureus*, monoclonal or polyclonal antibodies directed against the polysaccharide FN-R can be employed in methods to protect against infection caused by *S. aureus*. The patients at highest risk for developing a *S. aureus* infection can be predicted by use of the previously described diagnostic tests. Therefore, monoclonal antibodies directed against the FN-R may be administered in safe and effective amounts in methods which produce passive immunization in high risk patients.

Patients with the following clinical situations would benefit from the passive immunization with anti-FN-R monoclonal antibodies:

1) Patients undergoing prosthetic joint emplacement, especially those receiving artificial hips.
2) Patients receiving heart valves or other implanted devices.
3) Patients on hemodialysis or peritoneal dialysis.
4) Patients with recurrent *S. aureus* infections, especially patients that have diabetes mellitus, rheumatoid arthritis, and antibody deficiency syndromes.
5) Patients with major burns.
6) Immunosuppressed patients, especially those patients who are likely to have prolonged periods of neutropenia.
7) Patients who will have indwelling intravascular catheters, e.g., patients receiving hyperalimentation or chemotherapeutic agents.
8) Patients who have major orthopedic procedures, e.g., open reduction of fractures.

The availability of a diagnostic test using FN-R polysaccharide as an antigen, such as described in the ELISA test, to measure the pre-existing levels of antibody directed against the FN-R polysaccharide can help determine which patient will benefit from this passive immunization. However, the monoclonal antibody also can be of value in the treatment of *S. aureus* infections. Because the FN-R polysaccharide is expressed in the largest numbers on invasive *S. aureus* and because the FN-R polysaccharide is on the surface of the bacteria, the monoclonal antibody directed against this immunogen also can act as an opsonin as well as a blocking antibody. Hence, it is believed that passive immunization with this antibody decreases the severity of ongoing *S. aureus* infections, as well as, limits the ability of *S. aureus* to spread to new sites in the host. Thus, another use for the anti-FN-R monoclonal antibody is in a method of treating patients who already have *S. aureus* infections, especially those with bacteremia or those that are likely to develop bacteremia.

I have discovered that, in addition to the monoclonal antibodies to FN-R polysaccharide, the monoclonal antibodies to type 8 capsular polysaccharide of *S. aureus* can be used in the above described methods and diagnostic tests. These monoclonal antibodies are known and described in the publications of Nelles, et al, Infection and Immunity, Vol. 49, No. 1, July 1985, pp. 14–18 and Hochkeppel et al, Journal of Clinical Microbiology, Vol. 25, No. 3, March 1987, pp. 526–530, which are incorporated by reference herein. However, the uses of the monoclonal antibodies in the above described methods and diagnostic tests are new. The monoclonal antibodies are administered to animals to block or treat staphyloccecal infections by injecting sterile pharmaceutical preparations containing the monoclonal antibodies directly into the blood stream of the animals. The amount to be injected is an amount which is safe and effective as determined by the size and condition of the animal and the severity of its infection, if any.

It will be apparent to those skilled in the art that a number of modifications and changes may be made without departing from the spirit and scope of the invention. Therefore, it is intended that the invention not be limited except by the claims.

I claim:

1. A fibronectin receptor polysaccharide from *Staphylococcus aureus* which is useful as an antigen has the following identifying characteristics:
    (a) it is a polysaccharide which is primarily a carbohydrate having less than 2% protein and no lipids;
    (b) it contains aminohexoses;
    (c) it does not contain uronic acids;
    (d) it has a molecular weight of about 60 kdal;
    (e) it competes with intact organisms for fibronectin binding; and
    (f) it cross-reacts with monoclonal antibody directed at type 8 capsular material of *S. aureus*.

2. A method of preparing a fibronectin receptor polysaccharide which consists essentially of treating intact *Staphylococcus aureus* cells by sonification to remove the expressed fibronectin receptor polysaccharide on the cell surfaces without rupturing the cells and without killing the *S. aureus*, removing the bacteria material by centrifugation, separating the supernatant and subjecting it to DEAE ion exchange treatment and fibronectin affinity chromatography to obtain the desired product.

3. A fibronectin receptor polysaccharide prepared by the method of claim 2.

* * * * *